United States Patent [19]
Luther et al.

[11] Patent Number: 6,017,556
[45] Date of Patent: *Jan. 25, 2000

[54] LIPOSOMOGENIC UV ABSORBERS

[75] Inventors: Helmut Luther, Grenzach-Wyhlen; Dietmar Hüglin; Robert Hochberg, both of Freiburg, all of Germany

[73] Assignee: Ciba Specialty Chemicals Corporation, Tarrytown, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 08/931,392

[22] Filed: Sep. 16, 1997

[30] Foreign Application Priority Data

Sep. 17, 1996 [CH] Switzerland .............. 2273/96

[51] Int. Cl.[7] .............. A61K 9/127; A61K 7/06
[52] U.S. Cl. .............. 424/450; 424/70.1; 424/70.9; 514/880; 514/881; 514/944; 514/972
[58] Field of Search .............. 424/450, 59, 70.1, 424/70.9, DIG. 1; 514/880, 881, 944, 972

[56] References Cited

U.S. PATENT DOCUMENTS

| | | | |
|---|---|---|---|
| 4,290,974 | 9/1981 | Bouillon et al. | 260/511 |
| 4,406,880 | 9/1983 | Bouillon et al. | 424/40 |
| 4,585,597 | 4/1986 | Lang et al. | 260/507 |
| 5,505,936 | 4/1996 | Yano et al. | 424/60 |
| 5,605,704 | 2/1997 | Finel | 424/450 |
| 5,635,163 | 6/1997 | Hansenne | 424/60 |

FOREIGN PATENT DOCUMENTS

| | | |
|---|---|---|
| 1246446 | 12/1988 | Canada . |
| 0152379 | 8/1985 | European Pat. Off. . |
| 0629630 | 12/1994 | European Pat. Off. . |
| 2528420 | 12/1983 | France . |
| 2025957 | 1/1980 | United Kingdom . |
| 2209468 | 5/1989 | United Kingdom . |
| 9500111 | 1/1995 | WIPO . |

OTHER PUBLICATIONS

Makromol. Chem. 187, pp. 1843–1853, (1986).
J. Med. Chem. 1980, 23, pp. 50–59.
Chem. Abst. 85:192401f.
J. Am. Chem. Soc. 1993, 115, pp. 4387–4388.
Angew. Chem. Int. Ed. Engl. 31, (1992) pp. 709–726.
Chem. Abst. 112:119245e for JP 01,249,798.
Chem. Abst. 113:84846t for JP 01,249,717.

Primary Examiner—Gollamudi S. Kishore
Attorney, Agent, or Firm—Kevin T. Mansfield

[57] ABSTRACT

The use of liposomogenic UV absorbers for protecting human hair from the damaging effect of UV radiation is described. The liposomogenic UV absorbers comprise a hydrophilic head group (=Z), a spacer (=W), a UV chromophore (Q) having an absorption in the range from 285 to 400 nm and at least one hydrophobic tail group (=A). They have the formula

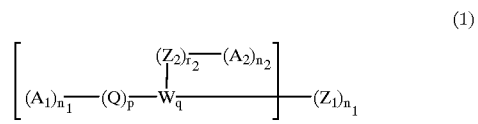

(1)

in which $A_1$ and $A_2$ independently of one another are a hydrophobic radical;

Q is a UV chromophore;

W is an organic radical;

$Z_1$ and $Z_2$ independently of one another are a hydrophilic radical; $n_1$ and $n_2$ independently of one another are a number from 0 to 4, where $n_1 = n_2 =$ is not included;

p is 1 or 2;

q is a number from 0 to 3;

$r_1$ is 1 or 2;

$r_2$ is 0 or 1; and $s_1$ is a number from 1 to 3.

The liposomogenic UV absorbers are capable of self-organization into bimolecular layers, and can as a result penetrate into the stratum corneum to a high degree and are extremely resistant to washing out there.

6 Claims, No Drawings

LIPOSOMOGENIC UV ABSORBERS

The present invention relates to the use of liposomogenic UV absorbers for protecting human hair from the damaging effect of UV radiation.

If human hair is exposed to sunlight for a relatively long period of time, various types of damage may occur. Dark hair acquires a reddish colour shade after some time, and blond hair becomes yellowish. The surface of the hair becomes rougher and at the same time drier. It also loses its shine in the course of time.

Hair can be protected effectively from harmful solar rays by using UV absorbers. Unfortunately, the UV absorbers used to date have an inadequate affinity for human hair, i.e. they can easily be washed out and therefore have only a short-term action.

Surprisingly, it has now been found that compounds which contain a UV chromophore having an absorption in the range from 285 to 400 nm and specific chemical structural elements which render these compounds capable of self-organization in bimolecular layers have a very good substantivity with respect to human hair and at the same time form an effective UV protection for the hair.

The present invention therefore relates to the use of liposomogenic UV absorbers which comprise a hydrophilic head group (=Z), a spacer (=W), a UV chromophore (Q) having an absorption in the range from 285 to 400 nm and at least one hydrophobic tail group (=A) for protecting human hair from the damaging effect of UV radiation.

The liposomogenic UV absorbers are those of the formula

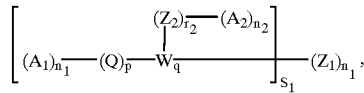
(1)

in which $A_1$ and $A_2$ independently of one another are a hydrophobic radical;

Q is a UV chromophore;

W is an organic radical;

$Z_1$ and $Z_2$ independently of one another are a hydrophilic radical; $n_1$ and $n_2$ independently of one another are a number from 0 to 4, where $n_1=n_2=0$ is not included;

p is 1 or 2;

q is a number from 0 to 3;

$r_1$ is 1 or 2;

$r_2$ is 0 or 1; and $s_1$ is a number from 1 to 3.

These compounds are synthetic amphiphilic compounds which are capable of organizing themselves, i.e. they spontaneously form a two-dimensional bilayer in water.

The hydrophobic radicals $A_1$ and $A_2$ are an alkyl, alkoxy, acyl or alkylamino radical in which the chains have at least 8 carbon atoms. Alkoxy radicals $A_1$ and $A_2$ are advantageously the radical of an unsaturated or, preferably, saturated aliphatic monoalcohol having 8 to 22 carbon atoms. The hydrocarbon radical can be branched or, preferably, straight-chain. $A_1$ and $A_2$ are preferably an alkyl or alkenyl radical having 10 to 14 carbon atoms.

Aliphatic saturated monoalcohols are naturally occurring alcohols, for example lauryl alcohol, myristyl alcohol, cetyl alcohol or stearyl alcohol, and synthetic alcohols, for example decyl alcohol, $C_{10}$–$C_{13}$oxo alcohol, tridecyl alcohol, isotridecyl alcohol or linear primary alcohols (Alfols) having 10 to 22 carbon atoms. Some representatives of these Alfols are Alfol (10–14), Alfol (12–13) or Alfol (16–18). ("Alfol" is a registered trade mark).

Unsaturated aliphatic monoalcohols are, for example, dodecenyl alcohol, hexadecenyl alcohol or oleyl alcohol.

The alcohol radicals can be present individually or in the form of mixtures, for example mixtures of alkyl and/or alkenyl groups which are derived from soya fatty acids, palm kernel fatty acids or tallow oils, of two or more components, preferably individually.

Alkylamino radicals $A_1$ and $A_2$ are derived from primary or, preferably, secondary $C_{12}$–$C_{22}$ fatty amines. These amines can be obtained from the corresponding fatty acids by dehydration and subsequent dehydrogenation. An alkylamino radical $A_1$ and $A_2$ is preferably a di-$C_{12}$–$C_{18}$alkylamino radical.

The acyl radical is preferably $C_8$–$C_{22}$alkylcarbonyl; for example octyl-, decyl-, dodecyl-, tridecyl-, hexadecyl- or octadecylcarbonyl.

Preferred liposomogenic UV absorbers are compounds of the formula (1) in which $n_1$ and $n_2$ are 1 or 2, preferably 2, and the radicals $A_1$ and $A_2$ have the same meaning.

The UV chromophore Q is derived from UV absorbers which are known per se. The liposomogenic UV chromophores according to the invention are preferably compounds having structural elements from the class of ($Q_1$) cinnamic acid esters;

($Q_2$) triazine derivatives;

($Q_3$) benzotriazoles;

($Q_4$) benzophenones;

($Q_5$) p-aminobenzoic acid derivatives; and ($Q_6$) benzylidenecamphor.

Preferred UV chromophores are ($Q_1$) cinnamic acid esters and ($Q_2$) triazine derivatives.

The cinnamic acid esters $Q_1$ are compounds of the formula

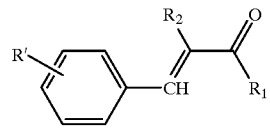
(2)

in which

R' is hydrogen, $C_1$–$C_4$alkyl; or $C_1$–$C_4$alkoxy;

$R_1$ is $C_1$–$C_4$alkoxy; preferably methoxy or ethoxy; and $R_2$ is hydrogen; $C_1$–$C_4$alkyl; or -CN.

Examples of compounds of the formula (2) are methyl or ethyl cinnamate.

The triazine derivatives $Q_2$ are, for example, hydroxyphenyl-s-triazines of the formula

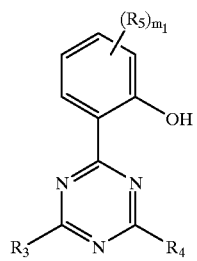

(3)

in which $R_3$ and $R_4$ independently of one another are $C_1$–$C_5$alkyl; $C_1$–$C_{18}$alkl which is substituted by hydroxyl, $C_1$–$C_5$alkoxy, $C_1$–$C_5$alkylthio, amino or $C_1$–$C_5$mono- or -dialkylamino; unsubstituted phenyl; or phenyl which is substituted by chlorine, hydroxyl, $C_1$–$C_{18}$alkyl and/or $C_1$–$C_{18}$alkoxy;

$R_5$ is $C_{1-C18}$alkyl; $C_1$–$C_{18}$alkoxy; halogen; hydroxyl; a radical of the formula

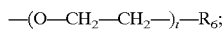

(3a)

or a radical of the formula

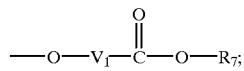

(3b)

$R_7$ is $C_1$–$C_5$alkyl or $C_1$–$C_5$alkoxy-$C_1$–$C_5$alkyl;

$V_1$ is a $C_1$–$C_4$alkylene radical;

$m_1$ is 0, 1 or 2;

t is 1 to 5; and $R_6$ is hydrogen; or $C_1$–$C_5$alkyl.

An alkyl group as the substituents $R_1$ to $R_6$ can be straight-chain or branched. Examples of such alkyl radicals are methyl, ethyl, n-propyl, isopropyl, n-butyl, isobutyl, sec-butyl, tert- butyl, pentyl, isopentyl, tert-pentyl, n-hexyl, 2-ethylhexyl, n-heptyl, n-octyl, isooctyl, n-nonyl, isononyl, n-dodecyl, heptadecyl or octadecyl.

Examples of $C_1$–$C_{18}$alkoxy or $C_1$–$C_5$alkylthio are, for example, methoxy, ethoxy, propoxy, isopropoxy, butoxy, isobutoxy, sec-butoxy, tert-butoxy, pentoxy, isopentoxy, n-heptyloxy, n-octyloxy, isooctyloxy, n-nonyloxy, isononyloxy, decyloxy, n-dodecyloxy, heptadecyloxy or octadecyloxy, and methylthio, ethylthio, propylthio, isopropylthio, butylthio, isobutylthio, sec- butylthio, tert-butylthio, pentylthio, isopentylthio or tert-pentylthio.

Examples of monoalkylamino are monomethyl-, monoethyl-, monopropyl-, monoisopropyl-, monobutyl- or monopentylamino. Examples of dialkylamino are dimethyl-, methylethyl- or diethylamino.

Halogen is, for example, fluorine, bromine or, preferably, chlorine.

Important s-triazine compounds are those of the formula

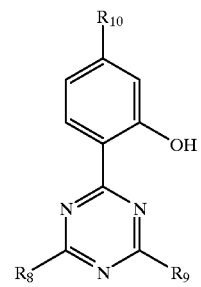

(4)

in which $R_8$ and $R_9$ independently of one another are phenyl which is unsubstituted or substituted by $C_1$–$C_5$alkyl and/or $C_1$–$C_5$alkoxy; and $R_{10}$ is hydrogen or $C_1$–$C_5$alkyl.

Other triazine compounds of interest are those of the formula

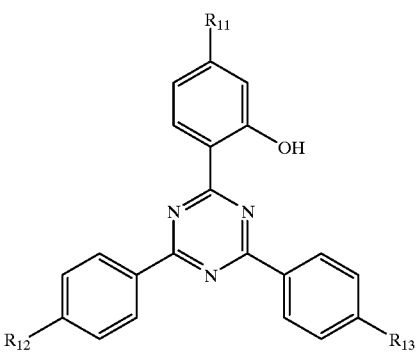

(5)

in which $R_{11}$ is hydrogen, hydroxyl, $C_1$–$C_{15}$alkyl, $C_1$–$C_{15}$alkoxy or a radical of the formula (3b) and $R_{12}$ and $R_{13}$ independently of one another are hydrogen or $C_1$–$C_{15}$alkoxy.

Hydroxyphenyl-s-triazines which are furthermore preferred are those of the formula (5) in which $R_{11}$, $R_{12}$ and $R_{13}$ independently of one another are $C_5$–$C_{15}$alkoxy, or those compounds in which $R_{11}$ is a radical of the formula (3b) and $R_{12}$ and $R_{13}$ are $C_5$–$C_{15}$alkoxy.

Suitable compounds of the formulae (3), (4) and (5) are, for example:

2-(2'-hydroxy-5'-methylphenyl)-4,6-dimethyl-s-triazine; melting point=131° C.;

2-(2'-hydroxy-3',5'-dimethylphenyl)-4,6-dimethyl-s-triazine; melting point=177° C.;

2-(2'-hydroxy-4',5'-dimethylphenyl)-4,6-dimethyl-s-triazine; λ=349 μm; T=48%;

2-(2'-hydroxy-4',5'-dimethylphenyl)-4,6-diethyl-s-triazine; melting point=98° C.;

2-(2'-hydroxy-5'-chlorophenyl)-4,6-dimethyl-s-triazine; melting point=160° C.;

2-(2'-hydroxyphenyl)-4,6-dimethyl-s-triazine; melting point=133° C.;

2-(2'-hydroxy-5'-tert-butylphenyl)-4,6-dimethyl-s-triazine; λ=352 μm; T=60%;

2-(2'-hydroxyphenyl)-4,6-didecyl-s-triazine; melting point= 53° C.;

2-(2'-hydroxyphenyl)-4,6-dinonyl-s-triazine; melting point= 45° C.;

2-(2'-hydroxyphenyl)-4,6-diheptadecyl-s-triazine; λ=338 mm; T=80%;

2-(2'-hydroxyphenyl)-4,6-dipropyl-s-triazine; melting point=18 to 20° C.;

2-(2'-hydroxyphenyl)-4,6-bis(β-methylmercaptoethyl)-s-triazine; λ=341 μm; T=60%;

2-(2'-hydroxyphenyl)-4,6-bis(β-dimethylaminoethyl)-s-triazine; λ=340 μm; T 63%;

2-(2'-hydroxyphenyl)-4,6-bis(β-butylaminoethyl)-s-triazine; λ=341 μm; T=66%;

2-(2'-hydroxyphenyl)-4,6-bis(β-butylaminoethyl)-s-triazine; λ=338 μm; T=68%;

2-(2'-hydroxyphenyl)-4,6-dioctyl-s-triazine; melting point= 40° C.;

2-(2'-hydroxy-4'-methoxyphenyl)-4,6-diphenyo-s-triazine; melting point=204–205° C.;

2-(2'-hydroxy-4'-ethoxyphenyl)-4,6-diphenyl-s-triazine; melting point=201–202° C.;

2-(2'-hydroxy-4'-isopropyl)-4,6-diphenyl-s-triazine; melting point=181–182° C.;

2-(2'-hydroxyphenyl)-4,6-bis(4-methoxyphenyl)-1,3,5-triazine;

2-(2'-hydroxyphenyl)-4,6-bis(4-methoxyphenyl)-1,3,5-triazine;

2-(2'-hydroxy-3'-methylphenyl)-4,6-bis(4-methoxyphenyl)-1,3,5-triazine;

2-(2',3'-dihydroxyphenyl)-4,6-bis(4-methoxyphenyl)-1,3,5-triazine;

2-(2'-hydroxy-5'-chlorophenyl)-4,6-bis(4-methoxyphenyl)-1,3,5-triazine;

2-(2'-hydroxy-4-methoxyphenyl)-4,6-bis(4-methoxyphenyl)-1,3,5-triazine;

2-(2',4'-dihydroxyphenyl)-4,6-bis(4-methoxypheny 1)-1,3,5-triazine;

2-(2'-hydroxy-4-hexyloxyphenyl)-4,6-bis(4-methoxyphenyl)-1,3,5-triazine;

2-(2'-hydroxy-4-hexyloxyphenyl)-4,6-bis(3-methoxyphenyl)-1,3,5-triazine;

2-(2-hydroxy-4-methoxyphenyl)-4-(4-methoxyphenyl)-6-phenyl-1,3,5-triazine;

2-(2'-hydroxy-4'-[2-ethylhexyloxy])-4,6-bis(2-ethythexyloxy)phenyl-1,3,5-triazine;

2-(2'-hydroxyphenyl)-4,6-bis(4-methoxyphenyl)-1,3,5-triazine;

2-(2',4'-dihydroxyphenyl)-4,6-bis(4-methoxyphenyl)-1,3,5-triazine;

2-(2'-hydroxy-3'-methylphenyl)-4,6-bis(4-methoxyphenyl)-1,3,5-triazine;

2-(2',3'-dihydroxyphenyl)-4,6-bis(4-methoxyphenyl)-1,3,5-triazine;

2-(2'-hydroxy-5'-chlorophenyl)-4,6-bis(4-methoxyphenyl)-1,3,5-triazine;

2-(2'-hydroxy-4-methoxyphenyl)-4,6-bis(4-methoxyphenyl)-1,3,5-triazine;

2-(2',4'-dihydroxyphenyl)-4,6-bis(4-methoxyphenyl)-1,3,5-triazine;

2-(2'-hydroxy-4-hexyloxyphenyl)-4,6-bis(4-methoxyphenyl)-1,3,5-triazine;

2-(2'-hydroxy-4-hexyloxyphenyl)-4,6-bis(3-methoxyphenyl)-1,3,5-triazine;

2-(2-hydroxy-4-methoxyphenyl)-4-(4-methoxyphenyl)-6-phenyl-1,3,5-triazine;

2-(2'-hydroxy-4'-[2-ethylhexyloxy])-4,6-bis(2-ethythexyloxy)phenyl-1,3,5-triazine;

4,6-bis(2-hydroxy-4-methoxyphenyl)-2-(2-propoxyethoxy)-1,3,5-triazine;

4,6-bis(2-hydroxy-4-propoxyphenyl)-2-(2-methoxyethoxy)-1,3,5-triazine;

4,6-bis(2-hydroxy-4-ethoxyphenyl)-2-(2-methoxyethoxy)-1,3,5-triazine;

4,6-bis(2-hydroxy-4-methoxyphenyl)-2-(2-methoxyethoxy)-1,3,5-triazine;

4,6-bis(2-hydroxy-4-methoxyphenyl)-2-(2-ethoxyethoxy)-1,3,5-triazine;

4,6-bis(2-hydroxy-4-methoxyphenyl)-2-[2-(2-ethoxyethoxy)ethoxy]-1,3,5-triazine;

4,6-bis(2-hydroxy-4-ethoxyphenyl)-2-(2-ethoxyethoxy)-1,3,5-triazine;

4,6-bis(2-hydroxy-4-ethoxyphenyl)-2-[2-(2-ethoxyethoxy)ethoxy]-1,3,5-triazine;

4,6-bis(2-hydroxy-4-ethoxyphenyl)-2-(2-ethoxy-2-methylethoxy)-1,3,5-triazine;

4,6-bis(2-hydroxy-4-ethoxyphenyl)-2-(ethoxymethoxy)-1,3,5-triazine;

4,6-bis(2-hydroxy-4-methoxyphenyl)-2-octyloxy-1,3,5-triazine;

4,6-bis(2-hydroxy-4-methoxyphenyl)-2-{2-[2-(2-ethoxy)ethoxy]ethoxy}ethoxytriazine;

4,6-bis(2-hydroxy-4-ethoxyphenyl)-2-{2-[2-(2-ethoxy)ethoxy]ethoxy}ethoxy-1,3,5-triazine; and 4,6-bis(2-hydroxy-4-ethoxyphenyl)-2-butoxy-1,3,5-triazine.

(T=percentage transmission of a solution of 1 mg of substance in 100 ml of chloroform at a layer thickness of 1 cm; λ[μm] is the maximum extinction coefficient).

The compounds of the formulae (3), (4) and (5) are known and can be prepared in a manner known per se, thus, for example, by heating an amidine and an o-hydroxybenzenecarboxylic acid ester, preferably in an approximate molar ratio of amounts of 2:1, in boiling, organic solvents [cf. U.S. Pat. No. 3,896,125 and Helv. Chim. Acta 55, 1566–1595 (1972)].

($Q_2$) structural elements of triazine UV absorbers which can furthermore be used are those of the formula (6)

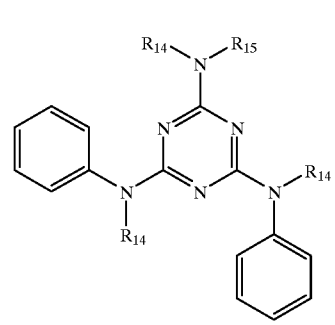

In this formula, $R_{14}$ and $R_{15}$ independently of one another are hydrogen, hydroxyl, $C_1$–$C_5$alkyl or $C_1$–$C_5$alkoxy.

The benzotriazoles $Q_3$ are compounds of the formula

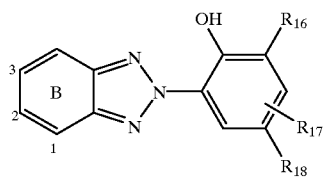
(7)

in which $R_{16}$ and $R_{18}$ independently of one another are hydrogen; $C_1$–$C_{18}$alkyl or $C_1$–$C_8$alkoxy which are unsubstituted or substituted by phenyl; halogen or the group

(7a)

in which $R_{19}$ is hydrogen; $C_1$–$C_{10}$alkyl; $C_5$–$C_8$cycloalkyl; $C_7$–$C_{10}$aralkyl; or $C_6$–$C_{10}$aryl; $R_{20}$ is hydrogen; $C_1$–$C_{20}$alkyl; $C_2$–$C_{17}$alkenyl; $C_5$–$C_8$cycloalkyl; $C_7$–$C_{10}$aralkyl or $C_6$–$C_{10}$aryl; and $t_2$ is 1 or 2, and, if $t_2$=1, $R_{19}$ and $R_{20}$ together with the ring bridge member

—N—CO— can also form a mono- or polynuclear nitrogen-containing heterocyclic radical, and in this case $R_{19}$ is —CO— or methylene which is unsubstituted or substituted by $C_1$–$C_5$alkyl and $R_{20}$ is $C_2$–$C_5$alkylene, $C_2$–$C_5$alkenylene, $C_6$–$C_{10}$arylene or vicinally bonded di-, tetra- or hexahydro-$C_6$–$C_{10}$arylene;

$R_{17}$ is $C_1$–$C_{18}$alkyl; $C_1$–$C_{18}$alkoxy; halogen; $C_6$–$C_{10}$aryl; $C_7$–$C_{10}$aralkyl; or $C_5$–$C_8$cycloalkyl; and the ring B can be substituted in positions 1, 2 and 3 by $C_1$–$C_5$alkyl, $C_1$–$C_5$alkoxy, carboxyl, $C_2$–$C_9$alkoxycarbonyl, $H_2NCO$—, $SO_2$—, $C_1$–$C_5$alkylsulfonyl or halogen or by the radical of the formula (7b)

$C_1$–$C_{10}$alkyl or $C_1$–$C_{20}$alkyl as the substituents $R_{19}$ and $R_{20}$ can be straight-chain or branched hydrocarbon radicals, for example methyl, ethyl, n-propyl, isopropyl, n-butyl, isobutyl, sec-butyl, tert-butyl, pentyl, isopentyl, tert-pentyl, n-hexyl, 2-ethylhexyl, n-heptyl, n-octyl, isooctyl, n-nonyl, isononyl, n-decyl, n-dodecyl, heptadecyl, octadecyl or eicosyl.

$C_6$–$C_{10}$Aryl $R_{19}$ and $R_{20}$ can be a mono- or bicyclic aromatic radical, for example phenyl or naphthyl.

$C_7$–$C_{10}$Aralkyl $R_{19}$ and $R_{20}$ are, for example, benzyl, phenethyl, α-methylphenethyl or α,α-dimethylbenzyl.

$C_5$–$C_8$Cycloalkyl $R_{19}$ and $R_{20}$ can be cyclopentyl, cycloheptyl, cyclooctyl or, preferably, cyclohexyl.

$C_2$–$C_{17}$Alkenyl radicals $R_{20}$ are, for example, vinyl, allyl, 1-propenyl, 2-butenyl, 2-pentenyl, 2-hexenyl, 2-decenyl, 3,6,8-decatrienyl or 2heptadecenyl.

Preferred benzotriazole compounds are those of the formula

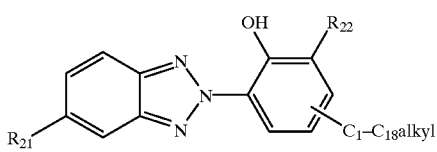
(8)

in which $R_{21}$ is $C_1$–$C_{18}$alkyl, or, preferably, hydrogen; and $R_{22}$ is $C_1$–$C_{18}$alkyl which is unsubstituted or substituted by phenyl.

Examples of benzotriazole compounds of the formulae (7) and (8) are:

2-(2'-hydroxy-5'-methylphenyl)benzotriazole;
2-(2'-hydroxy-5-tert-butylphenyl)benzotriazole;
2-(2'-hydroxy-3'-tert-butyl-5'-methylphenyl)-5-chlorobenzotriazole;
2-(2'-hydroxy-3',5'-di-tert-butylphenyl)-5-chlorobenzotriazole;
2-(2'-hydroxy-5'-tert-octylphenyl)benzotriazole;
2-(2'-hydroxy-3'-acryloylamidomethyl-5'-methylphenyl)benzotriazole;
2-(2'-hydroxy-3'-acryloylamidomethyl-5'-benzylphenyl)benzotriazole;
2-(2'-hydroxy-3'-butoxacetamidomethyl-5'-benzylphenyl)benzotriazole;
2-(2'-hydroxy-3',5'-di-tert-amylphenyl)benzotriazole; and
2-(2'-hydroxy-3',5'-di-tert-butylphenyl)benzotriazole.

The benzotriazole compounds of the formulae (7) and (8) which are known to be UV-absorbing are for the most part described in FR-A-1 195 307 or U.S. Pat. No. 3,629,192.

The benzophenones ($Q_4$) are compounds of the formula

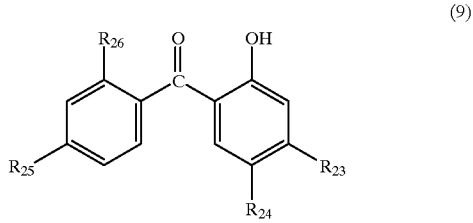
(9)

in which $R_{23}$ is hydrogen, hydroxyl, $C_1$–$C_{14}$alkoxy, phenoxy or amino; where $C_1$–$C_{14}$alkoxy can be substituted by a radical of the formula

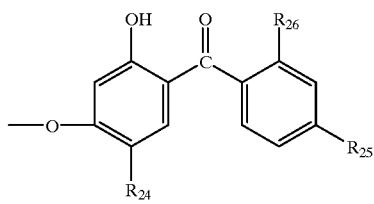

(9a)

and/or an acyloxy radical;

$R_{24}$ is hydrogen, halogen or $C_1$–$C_5$alkyl;
$R_{25}$ is hydrogen, hydroxyl or $C_1$–$C_5$alkoxy; and
$R_{26}$ is hydrogen or hydroxyl.

Acyl is $C_1$–$C_5$alkanoyl, for example formyl, acetyl, propionyl, acryloyl, methacryloyl or benzoyl.

The compounds of the formula (9) can be prepared by processes which are known per se, such as are described, for example, in U.S. Pat. Nos. 3,468,938, 3,696,077 and 4,698,064.

The UV chromophores ($Q_5$) are para-aminobenzoic acid derivatives of the formula

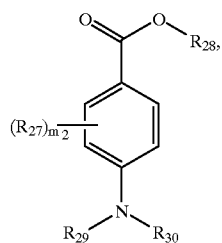

(10)

in which $R_{27}$ is hydroxyl; halogen; cyano; $C_1$–$C_5$alkyl; $C_1$–$C_5$alkoxy; mono-$C_1$–$C_5$alkylamino; di-$C_1$–$C_5$alkylamino;
$R_{28}$ is hydrogen; or $C_1$–$C_5$alkyl;
$R_{29}$ and $R_{30}$ independently of one another are hydrogen; or $C_1$–$C_5$alkyl; and
$m_2$ is 0, 1 or 2.

UV chromophores ($Q_5$) which are preferably employed are structural elements which are derived from para-aminobenzoic acid or the methyl or ethyl ester thereof.

UV chromophores ($Q_6$) are benzylidenecamphors. They are those of the formula

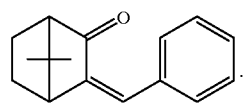

(11)

For the preparation of the liposomogenic UV absorbers according to the invention, the UV chromophores ($Q_1$)–($Q_6$) in question are employed as aqueous dispersions, provided that they are compounds which are sparingly soluble in water.

Various compounds are suitable dispersing agents here, for example acid esters or their salts of alkylene oxide adducts, polystyrenesulfonates, fatty acid taurides, alkylated diphenyl oxide mono- or disulfonates, sulfonates of polycarboxylic acid esters, or the addition products, converted into an acid ester with an organic dicarboxylic acid or an inorganic polybasic acid, of 1 to 60, preferably 2 to 30 mol of ethylene oxide and/or propylene oxide on fatty amines, fatty amides, fatty acids or fatty alcohols having in each case 8 to 22 carbon atoms or on tri- to hexahydric alkanols having 3 to 6 carbon atoms, ligninsulfonates and formaldehyde condensation products. Details on the dispersing agents and the preparation of the UV absorber dispersions are to be found, for example, in EP-A-0 523 006.

The following chromophores Q are preferably employed according to the invention:

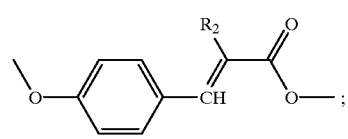

(2a)

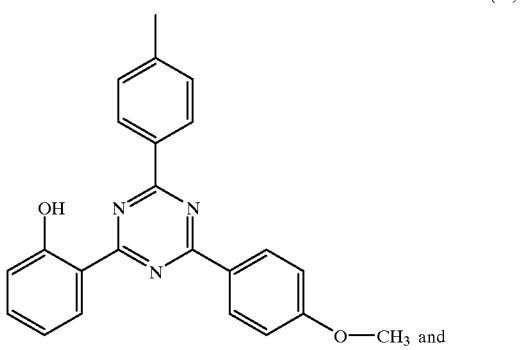

(6a)

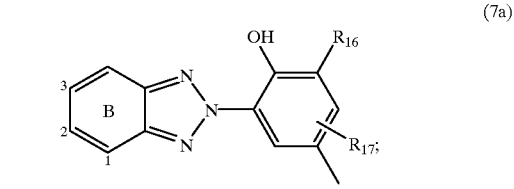

(7a)

in these formulae, $R_2$, $R_{14}$, $R_{16}$, $R_{17}$ and B are as defined in the formulae (2), (6) and (7).

The organic radical W is as a rule an alkylene radical which is at least divalent and can be uninterrupted or interrupted by a carbonyl, carbonylato or ether group. W is, in particular, a branched or, preferably, straight-chain alkylene group having 1 to 8, preferably 2 to 5 carbon atoms. It is, for example, the —$CH_2$—; —$CH_2CH_2$—;

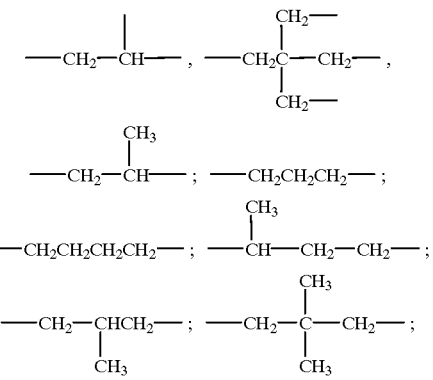

—$CH_2(CH_2)_4CH_2$—; —$CH_2(CH_2)_6CH_2$—; —$CH_2$—(CO)O—$CH_2$—; —$CH_2$—(CO)—$CH_2$—; —(CO)O—$CH_2$—or the —CH=CH–CH$_2$- group.

Hydrophilic radicals Z, and Z$_2$ are, preferably, (Z$_a$) ammonium or amine compounds;

(Z$_b$) phosphate compounds;

(Z$_c$) carboxylate compounds;

(Z$_d$) polyols; and (Z$_e$) sulfate compounds.

They form the hydrophilic head groups of the liposomogenic UV absorbers according to the invention. In these structural elements, a distinction may be made between cationic (Z$_a$), anionic ((Z$_b$), (7,), (Z$_e$)) and neutral head groups ((Z$_a$) and (Z$_d$)).

Cationic ammonium compounds (Z$_a$) are, in particular, mono- or di-C$_1$–C$_5$-alkylammonium compounds, which can be modified by further substituents. Examples which may be mentioned are the following groups:

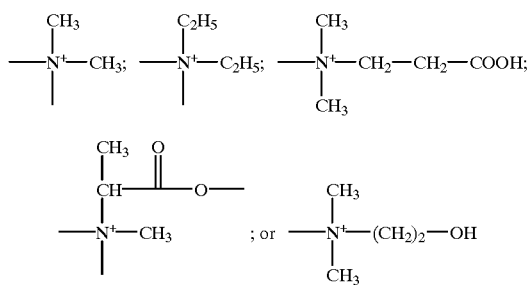

Neutral amine compounds are, for example, the groups

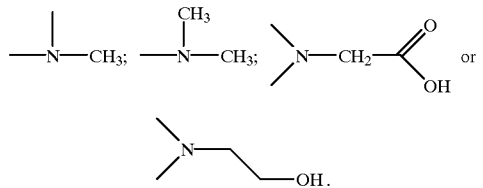

Phosphate groups Z$_b$ are, in particular, compounds which are derived from mono- and diesters of phosphoric acid. The phosphorus compounds are usually used here in the form of their sodium salts.

The carboxylate compounds (Z$_c$) are derived from lower mono- or dicarboxylic acids and are likewise usually used as sodium salts.

Polyols (Z$_e$) are, for example, the following compounds:

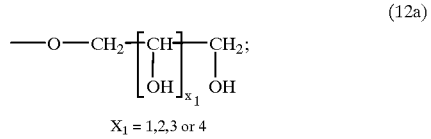

(12a)

X$_1$ = 1,2,3 or 4

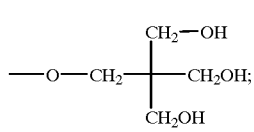

(12b)

(12c)

(12d)

; and (12e)

The sulfate compounds (Z$_e$) are derived from alkyl sulfates, which can be unsubstituted or else further substituted. Sulfate groups are, primarily, the sulfate ion, SO$_4^{2-}$.

The head groups (Z$_a$)—(Z$_e$) can simultaneously form the unit —W—Z$_1$ or —W—Z$_2$—with the organic radical W, depending on which starting compounds are used.

The liposomogenic UV absorbers employed according to the invention can be prepared by methods which are known per se. As a rule, they are prepared by a planned sequence of reaction steps which are known per se, such as condensation, alkyation, esterification, hydrolysis and the like. Information on carrying out the reactions can be found from monographs for organic synthesis, for example J. March, Advanced Organic Chemistry, 2nd Edition, McGraw-Hill, New York, 1977.

The hydrophobic radicals A can be introduced in very different ways, for example by etherification of the phenolic OH group of the UV chromophore (cf. Examples 1, 2, 5 and 7), or by reaction of an acid chloride with a long-chain dialkylamine (cf. Example 4). A large number of reactions are also suitable for introduction of the hydrophilic head groups Z, as can be seen from Examples 1 and 2 (quaternization). With a suitable reaction procedure, however, A and Z can also be introduced simultaneously, i.e. in one reaction step. This is achieved, for example, by opening a suitable acid anhydride with a fatty alcohol (Example 6).

Especially preferred liposomogenic compounds are those of the formula $$[(A_1)n_1(Q)_p(W_q)_2]—(Z_{1r_1}) \quad (13)$$

in which

A$_1$ is a hydrophobic radical;

Q is a UV chromophore;

W is an organic radical;

Z$_1$ is a hydrophilic radical;

$n_1$ is a number from 1 to 4;

p is 1 or 2;

q is 1 to 3;

$r_1$ is 1 or 2; and $S_2$ is 1 to 3.

Compounds which are furthermore preferred are those of the formula

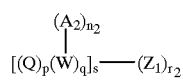
(14)

in which $A_2$ is a hydrophobic radical;

Q is a UV chromophore;

W is an organic radical;

$Z_1$ is a hydrophilic radical;

$n_2$ is 1 or 2;

p is 1 or 2;

q is 1 to 3;

$r_2$ is 1 or 2; and s is 1 or 2.

Preferred compounds among the liposomogenic UV absorbers according to the invention which contain a structural element of a cinnamic acid derivative as the UV chromophore are those of the formula

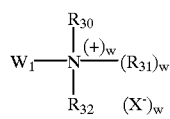
(15)

in which $W_1$ is a radical of the formula

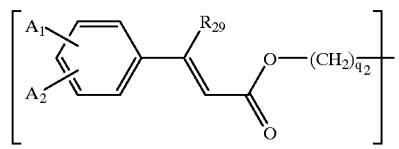
(15a)

$R_{29}$ is hydrogen; $C_1$–$C_4$alkyl or —CN;

$R_{30}$ and $R_{31}$ independently of one another are $C_1$–$C_5$alkyl, hydroxyl, hydroxy-$C_1$–$C_5$alkyl or carboxyl;

$R_{32}$ is $C_1$–$C_5$alkyl; hydroxyl; hydroxy-$C_1$–$C_5$alkyl; carboxyl; or a radical of the formula (15a);

$A_1$ and $A_2$ independently of one another are hydrogen or a $C_{10}$–$C_{14}$alkoxy radical, one radical always being a $C_{10}$–$C_{14}$alkoxy radical;

X is a halogen atom;

q is a number from 2 to 4; and w is 0 or 1;

or compounds of the formula

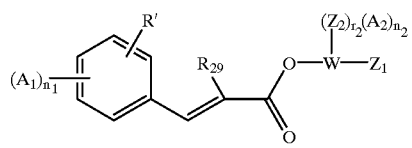
(16)

in which $R_{29}$ is hydrogen; $C_1$–$C_4$alkyl or -CN;

R' is hydrogen, $C_1$–$C_4$alkyl; or $C_1$–$C_4$alkoxy;

$A_1$ and $A_2$ independently of one another are a $C_{10}$–$C_{14}$alkoxy radical;

W is a $C_2$–$C_4$alkylene radical which is uninterrupted or interrupted by a —O(CO)—group; and $Z_1$ and $Z_2$ independently of one another are the radical of a $C_1$–$C_3$carboxylic acid;

$n_1$ and $n_2$ independently of one another are 0, 1 or 2, where $n_1=n_2=0$ is not included; and $r_2$ is 1 or 2.

Preferred liposomogenic UV absorbers according to the invention which contain a triazine radical as the UV chromophore are those of the formula

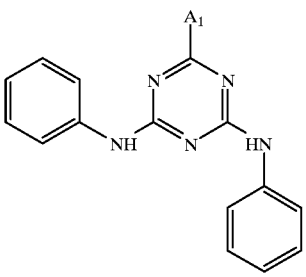
(17)

in which $A_1$ is a radical of the formula

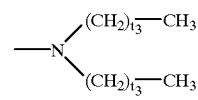
(17a)

or of the formula

O—(CH$_2$)$_{t_4}$—CH$_3$ (17b)

and $t_3$ and $t_4$ independently of one another are a number from 5 to 13.

Further preferred liposomogenic UV absorbers according to the invention which contain a triazine radical as the UV chromophore are those of the formula

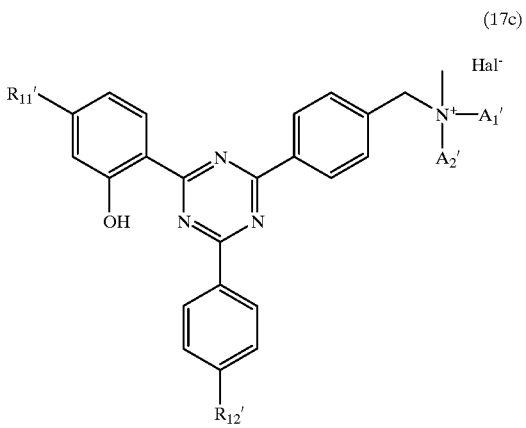

(17c)

in which
R$_1$' is hydrogen, hydroxyl, C$_1$–C$_{15}$alkyl or C$_1$–C$_{15}$alkoxy and
R$_{12}$' is hydrogen or C$_1$–C$_{15}$alkoxy;
A$_1$' and A$_2$' independently of one another are C$_8$–C$_{22}$alkyl; and Hal is halogen.

Preferred liposomogenic UV absorbers according to the invention which contain a benzylidenecamphor as the UV chromophore are those of the formula

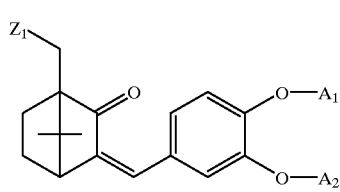

(18a)

or of the formula

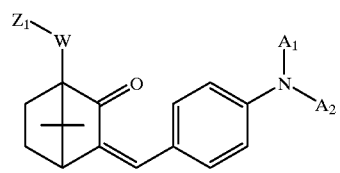

(18b)

in which
A$_1$ and A$_2$, W and Z, are as defined in formula (1).

The liposomogenic UV absorbers employed according to the invention are distinguished by the fact that they have
a high substantivity for human hair
and guarantee a high UV protection for hair.

The invention also relates to a hair cosmetics preparation comprising at least 0.25 to 5% by weight, based on the total weight of the composition, of a liposomogenic UV absorber of the formula (1) and at least one auxiliary which is tolerated by the skin and hair.

The hair cosmetics composition can be prepared by physical mixing of the liposomogenic UV absorber or absorbers with the auxiliary or auxiliaries by the usual methods, for example by simple stirring together of the individual components.

For use in hair cosmetics, the UV absorbers according to the invention usually have an average particle size in the range from 0.02 to 2, preferably 0.05 to 1.5, and especially from 0.1 to 1.0 μm, provided that they are not water-soluble. The insoluble UV absorbers according to the invention can be brought to the desired particle size by customary methods, for example grinding with, for example, a jet, ball, vibratory or hammer mill. Grinding is preferably carried out in the presence of 0.1 to 30, preferably 0.5 to 15% by weight, based on the UV absorber, of a grinding aid, for example an alkylated vinylpyrrolidone polymer, a vinylpyrrolidonelvinyl acetate copolymer, an acylglutamate or, in particular, a phospholipid.

Any emulsifier which can be employed conventionally can be used for the preparation of the hair cosmetics formulations according to the invention, for example one or more ethoxylated esters of naturally occurring derivatives, for example polyethoxylated esters of hydrogenated castor oil; or a silicone oil emulsifier, for example silicone polyol; a nonethoxylated or ethoxylated fatty acid soap; an ethoxylated fatty alcohol; a nonethoxylated or ethoxylated sorbitan ester; an ethoxylated fatty acid or an ethoxylated glyceride.

The hair cosmetics preparation here can be
in the form of a shampoo, a lotion, a gel or an emulsion for rinsing, before or after shampooing, before or after dyeing or bleaching, or before or after a permanent wave or a straightening operation,
in the form of a lotion, a foam or a gel for styling or treatment,
in the form of a lotion or a gel for brushing or for waving,
in the form of a hair lacquer,
in the form of a composition for a permanent wave or for straightening, or for dyeing or for bleaching the hair.

The following hair cosmetics formulations, for example, can be used:

a$_1$) spontaneously emulsifying stock formulation comprising the UV absorber, PEG 6–C$_{10}$oxo alcohol and sorbitan sesquioleate, to which water and any desired quaternary ammonium compound, for example 4% of minkamidopropyldimethyl-2-hydroxyethylammonium chloride or Quaternium 80 are added;

a$_2$) spontaneously emulsifying stock formulation comprising the UV absorber, tributyl citrate and PEG 20–sorbitan monooleate, to which water and any desired quaternary ammonium compound, for example 4% of minkamidopropyldimethyl-2-hydroxyethylammonium chloride or Quaternium 80, are added;

b) quat-doped solutions of the UV absorber in butyltriglycol and tributyl citrate;

c) dispersions of micronized UV absorbers obtained by known methods (precipitation from solutions or solution mixtures, grinding) and having an average diameter of 0.05–1.0 mm in APG (for example Plantaren) and a quat compound (for example minkamidopropyl-2-hydroxyethylammonium chloride) in an aqueous formulation;

d) mixtures or solutions of the UV absorber with N-alkylpyrrolidone.

In addition to the liposomogenic UV absorbers according to the invention, the hair cosmetics preparation can also additionally comprise one or more other UV protection substances, for example oxanilides or vinyl group-containing amides or cinnamic acid amides. Such protection substances are described, for example, in GB-A-2 286 774 or are known from Cosmetics & Toiletries (107), 50 et seq. (1992).

The compositions according to the invention can furthermore also comprise other beneficial auxiliaries, for example surface-active agents, thickeners, polymers, preservatives, fragrances, foam stabilizers, electrolytes, organic solvents, oils, waxes, degreasing agents, dyes and/or pigments, which serve to impart to the hair cosmetics composition the same shading as the hair to be treated, and other auxiliaries customary in hair cosmetics.

The present invention also relates to a process for the treatment of human hair for protection from the damaging effect of UV radiation. The process comprises treating the hair with a shampoo, a lotion, a gel or an emulsion for rinsing, before or after shampooing, before or after dyeing or bleaching or before or after a permanent wave or a straightening operation, with a lotion, a foam or a gel for styling, with a lotion, a foam or a gel for brushing or for waving, with a hair lacquer or with a composition for a permanent wave or for straightening, or for dyeing or bleaching the hair, the shampoo, the lotion, the gel, the emulsion, the hair lacquer or the composition for a permanent wave comprising a liposomogenic UV absorber of the formula (1).

The following examples serve to illustrate the invention without limiting it thereto.

PREPARATION EXAMPLES FOR THE NOVEL COMPOUNDS

EXAMPLE 1 bis{2-[3-(4-Dodecyloxyphenyl)acryloyloxy]ethyl}dimethylammonium methyl sulfate coumaric acid with dodecyl bromide. The colourless crystals have a melting point of 158–159° C. The corresponding acid chloride is obtained therefrom virtually quantitatively by reaction with oxalyl chloride in benzene (18 hours, room temperature).

28.1 g (0.08 mol) of 4-dodecyloxycinnamyl chloride are initially introduced into 150 ml of chloroform, and first 4.1 g (0.04 mol) of triethylamine and then 5.0 g (0.04 mol) of N-methyl-diethanolamine are added, while stirring and cooling at room temperature. The mixture is subsequently stirred for about 4 hours and cooled to 10° C. and, for liberation of the base, the reaction solution is added dropwise to 250 ml of chloroform, which has been saturated with $NH_3$ beforehand. The suspension is filtered twice over Hyflo® and evaporated to dryness. The crude amine can be purified by column chromatography (silica gel, toluene/ethanol 95/5). The yield is 53% of theory.

For quaternization, the amine is initially introduced into toluene and is reacted with the molar amount of dimethyl sulfate (=101a) or methyl iodide (=101b) at 40° C. After 3 hours, the thin layer chromatogram is free from starting material. The mixture is evaporated to dryness in vacuo and acetone is added to the residue, for crystallization. The colourless crystals are washed with acetone and then with hexane and dried at 40° C. The quaternization proceeds virtually quantitatively.

UV spectrum ($10^{-5}$M; ethanol):$\lambda_{max}$=313 nm $\epsilon_{max}$=53,500 $M^{-1}cm^{-1}$

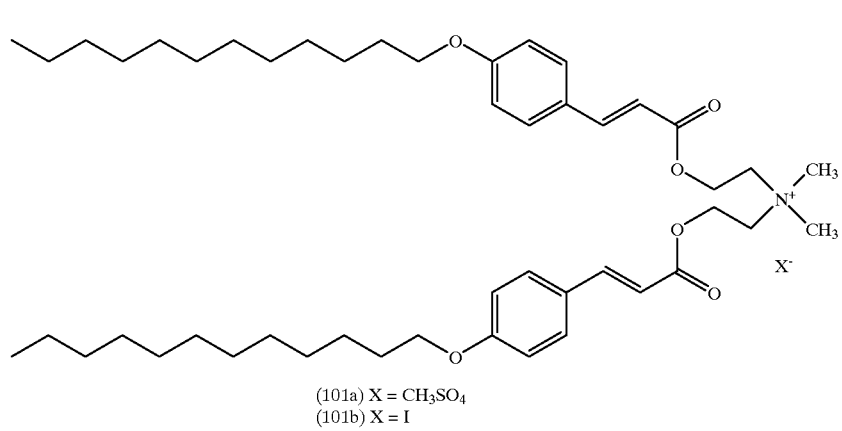

(101)

(101a) X = $CH_3SO_4$
(101b) X = I

4-Dodecyloxycinnamic acid is prepared by generally known processes by condensation of a 4-alkoxybenzaldehyde with malonic acid or by reaction of

EXAMPLE 2

{2-[3- (3,4-Bisdodegyloxyphenyl)acryloyloxy]
ethyl}-(2-hydroxyethyl)dimethyl-ammonium
bromide

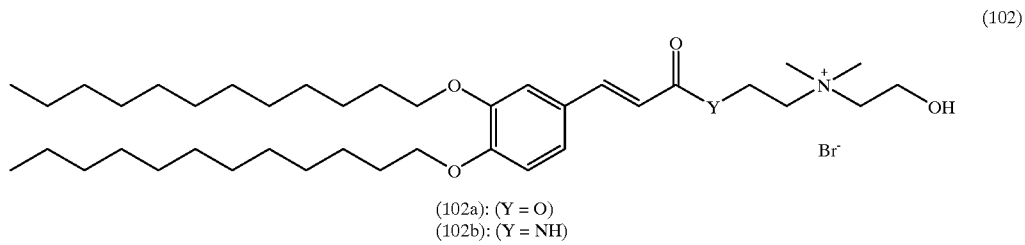

(102a): (Y = O)
(102b): (Y = NH)

3,4-Bisdodecyloxycinnamic acid and the corresponding acid chloride are prepared in analogy to the process described in Example 1. For esterification and liberation of the amine base, the reaction is likewise carried out with 2-dimethylaminoethanol analogously to Example 1.

The quaternization with 2-bromoethanol was carried out in toluene at 100° C. in the course of 12 hours. The crude product can be further purified by washing with acetone and subsequent column chromatography.

UV spectrum ($10^{-5}$M; ethanol):$\lambda_{max}$=328 nm $\epsilon_{max}$=19,500 $M^{-1}$ $cm^{-1}$

EXAMPLE 3

{2-[3-(3,4-Bisdodecyloxyphenyl)acryloylamino]
ethyl}-(2-hydroxyethyl)dimethyl-ammonium
bromide The synthesis of this compound is carried out in accordance with the process described in Example 2. Instead of the esterification, reaction with 2-dimethylaminoethylamine to give the amide is carried out. The product can be purified by trituration with acetone and recrystallization from methanol.

UV spectrum ($10^{-5}$M; ethanol):$\lambda_{max}$=321 nm $\epsilon_{max}$=19,500 $M^{-1}cm^{-1}$

EXAMPLE 4

2,4-Bis[(4-carboxyl)anilino]-6-dioctadecylamino-s-
triazine (sodium salt)

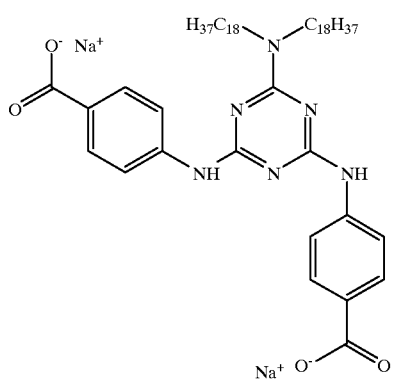

(104)

18.5 g (0.1 mol) of cyanuric chloride are initially introduced into 250 ml of a dioxane/water (9/1) mixture at 0–5° C. 16.5 g (0.1 mol) of ethyl 4-aminobenzoate are introduced, while stirring, and the temperature is allowed to rise to 15° C., the pH falling to 0.5. The white suspension is brought to a pH of 8.0–8.5 with 30% NaOH, and a further equivalent of amine is added. The mixture is diluted with 250 ml of dioxane/water and heated to 90° C., the pH being kept at 8.5 by automatic metering in of NaOH. After 4 hours, the solid is filtered off with suction and washed with dioxane, water and methanol. The crude intermediate is purified by recrystallization from ethylcellosolve (yield: 25.7 g; 58% of theory; melting point 264° C.).

6.63 g (0.015 mol) of the intermediate and 1.83 g (0.015 mol) of 4-(dimethylamino)pyridine are initially introduced into 70 ml of dimethylformamide, and 8.3 g of dioctadecylamine, dissolved in 30 ml of chloroform, are added at 60° C. The mixture is stirred at 100° C. for 3 hours and the hot solution is filtered and evaporated to dryness. The residue is extracted with 50 ml of toluene/ethyl acetate (80/20) and purified by column chromatography (silica gel) (yield: 4.5 g; 33% of theory; colourless, waxy ester).

For the hydrolysis, the ethyl ester is initially introduced into an ethanol/NaOH mixture and the mixture is heated under reflux for 2 hours. The gelatinous precipitate is filtered off and washed with acetone. The hydrolysis takes place virtually quantitatively.

UV spectrum ($10^{-5}$M; ethanol): $\lambda_{max}$=301 nm $\epsilon_{max}$=60,000 $M^{-1}cm^{-1}$

EXAMPLE 5

Mono{3-[3-(3,4-bisdodecyloxyphenyl)acryloyloxy]-2-hydroxypropyl}2,3-diacetoxnsuccinate

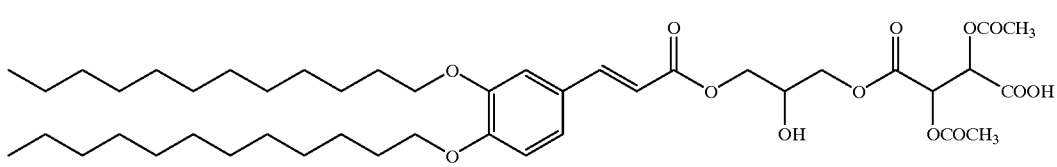

(105)

3,4-Bisdodecyloxycinnamic acid and the corresponding acid chloride are prepared analogously to the process described in Example 1. The monoglyceride is obtained therefrom in a virtually quantitative yield in accordance with instructions by Watanabe et al. (J. Med. Chem. 1980, 23, 50–59) by esterification with isopropylideneglycerol and subsequent splitting off of the protective group with boric acid.

A mixture of 5.91 g (0.01 mol) of monoglyceride and 2.16 g (0.01 mol) of diacetyltartaric anhydride is heated at 120° C. under an inert gas for 2 hours. The vitreous crude product can be purified by column chromatography (silica gel; toluene/acetone 8/2).

UV spectrum ($10^{-5}$M; ethanol): $\lambda_{max}$=328 nm $\epsilon_{max}$=17,400 $M^{-1}cm^{-1}$

EXAMPLE 6

1-Dodecyl 2-[3-(4-dodecyloxyphenyl)acryloxy]succinate

4-Dodecyloxycinnamyl chloride is prepared as described in Example 1.

30.9 g (0.088 mol) of the acid chloride are initially introduced into the reaction vessel together with 5.36 g (0.04 mol) of DL-malic acid and 100 ml of chlorobenzene and the mixture is heated to 130° C. under an inert gas. After the mixture has been stirred for 2 hours, the evolution of HCl has ended. 7.7 g (0.04 mol) of 1-dodecanol, dissolved in 10 ml of chlorobenzene, are now added dropwise and the mixture is stirred under reflux for a further 3 hours. After cooling, the precipitate is filtered off with suction, washed with toluene and hexane and dried at 80° C. in vacuo. The crude product can be purified by column chromatography (silica gel, toluene/acetone 80/20). The yield is 15.2 g (62% of theory).

UV spectrum ($10^{-5}$M; ethanol): $\lambda_{max}$=311 nm $\epsilon_{max}$=27,300 $M^{-1}$ $cm^{-1}$

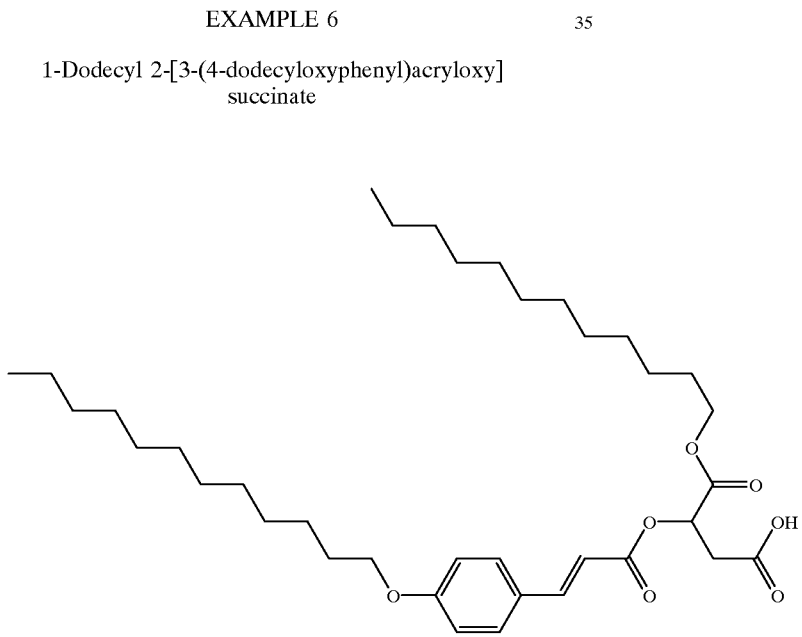

(106)

EXAMPLE 7

Bis{2-[3-(4-dodecyloxyphenyl)acryloyloxy]ethyl}aminoacetic acid

UV spectrum ($10^{-5}$M; ethanol): $\epsilon_{max}$=312 nm $\epsilon_{max}$=26, 400 M$^{-1}$ cm$^{-1}$

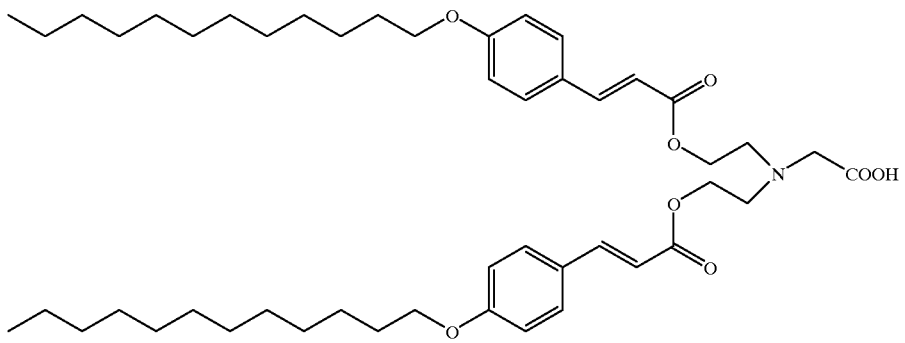

(107)

26.7 g (0.075 mol) of 4-dodecyloxycinnamyl chloride (for the preparation, see Example 1.) and 4.9 g (0.03 mol) of N,N-bis(hydroxyethyl)glycine are mixed thoroughly and are heated slowly to 130–140° C. under an inert gas. The batch becomes stirrable above 80° C., and evolution of HCl occurs. The reaction has ended after 4 hours. After cooling, 100 ml of acetone/water (95/5) are added and the batch is heated under reflux for 2 hours. It is evaporated to dryness and purified by column chromatography (silica gel, toluene/acetone 80/20). The yield of the highly hygroscopic product is 3.1 g (13% of theory).

UV spectrum ($10^{-5}$M; ethanol): $\lambda_{max}$=313 nm $\epsilon_{max}$=29, 300 M$^{-1}$ cm$^{-1}$

EXAMPLE 8

1-{2-[3-(4–Methoxyphenyl)acryloxy]ethyl}2-dodec-2-enylsuccinate

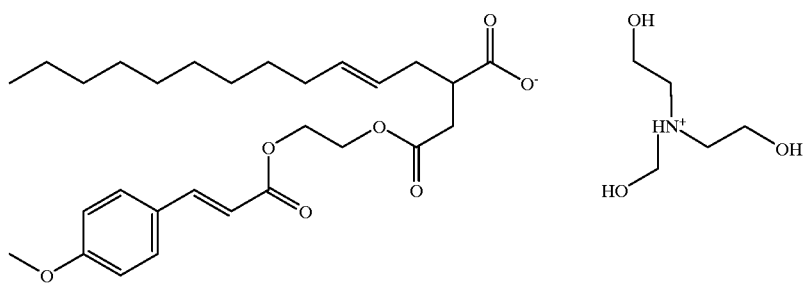

(108)

2-Hydroxyethyl 4-methoxycinnamate is prepared by methods known from the literature (esterification).

9.0 g (0.04 mol) of 2-hydroxyethyl 4-methoxycinnamate and 10.6 g (0.04 mol) of 2-dodecenylsuccinic anhydride are dissolved in 50 ml of toluene and the solution is stirred at 100–110° C. After 6 hours, the thin layer chromatogram shows a virtually quantitative conversion. The batch is cooled to 55–60° C. and 5.35 g (0.036 mol) of triethanolamine are added. The mixture is subsequently stirred for 6 hours and the solvent is removed in vacuo. 24.9 g (97.7% of theory) of the slightly coloured, highly viscous product are obtained.

EXAMPLE 9

1-{[1-Hydroxy-2-(2-benzotriazolyl)-6-t-butyl-4-(4-hydroxybutyl)]phenyl}2-dodec-2-enylsuccinate (109)

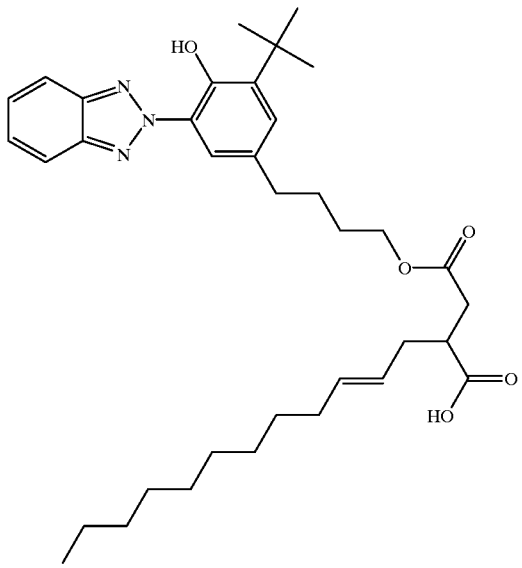

2-Benzotriazol-2-yl-6-t-butyl-4-(4-hydroxybutyl)phenol is prepared by methods known from the literature.

8.5 g (0.025 mol) of 2-benzotriazol-2-yl-6-t-butyl-4-(4-hydroxybutyl)phenol and 6.9 g (0.025 mol) of 2-dodecenylsuccinic anhydride are dissolved in 100 ml of toluene and the solution is stirred under nitrogen at 100–110° C. After 18 hours, the thin layer chromatogram shows a virtually quantitative conversion. The solvent is removed in vacuo and purified by column chromatography (toluene/ethyl acetate=9/1; silica gel 40×5 cm). 5.4 g of a slightly coloured, highly viscous product are obtained (36% of theory).

UV spectrum ($10^{-5}$M; ethanol): $I_{max}$=340nm $I_{max}$=14,500 $M^{-1}cm^{-1}$

EXAMPLE 10a

2-[4-Hydroxymethylphenyl]-4-[4-methoxyphenyl]-6-[2-hydroxyphenyl]-s-triazine 12.7 g of the benzoxazinone of the formula (110a)

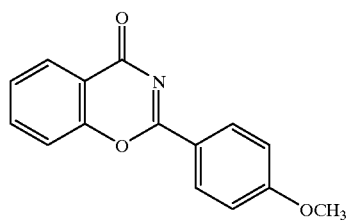

(prepared by the method of Brunetti,Lüithi; Helv. 55 (1972) 1566–1595) and 9.3 g of the benzamidine hydrochloride of the formula (110b)

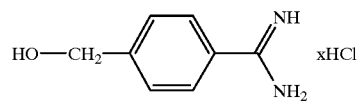

(mentioned in DE 3509010) are stirred into 300 ml of methanol to give a white suspension. 9 g of sodium methylate solution (30% in methanol) are added dropwise to this mixture at room temperature under nitrogen in the course of 10 minutes, and the mixture is stirred at 70° C. for 2 hours. After cooling, the solid is filtered off with suction, washed with 50 ml of methanol and 200 ml of water and dried at 60° C. in vacuo. 14.5 g of the compound of the formula (110c)

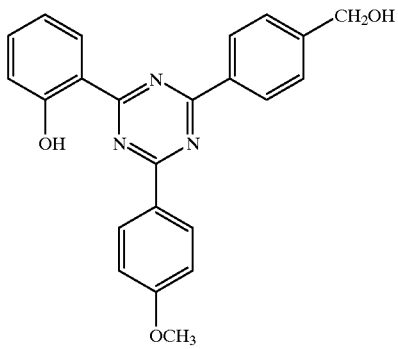

are obtained as a pale yellow powder (yield 75.2%).

Physical data:

Melting point 240.4° C. UV (acetonitrile): $\lambda_{max}$ 279 nm/$\epsilon$40300

EXAMPLE 10

2-[4-Didecylaminomethyl]-4-[4-methoy]-6-[2-hydroxyhenyl]-s-triazine 7.7 g of the compound of the formula (110c) are stirred into 100 ml of chlorobenzene to give a yellow suspension and this is heated to about 100° C. 2.85 g of thionyl chloride are added at this temperature, after which a yellow clear solution forms. The solution is stirred at 100° C. for 2.5 hours. 30 ml of liquid are then distilled off at a bath temperature of 160° C. After cooling to 110° C., 6.6 g of didecylmethylamine are added dropwise, and the mixture is stirred overnight and then left to stand to crystallize out. The crystals formed (unreacted intermediate of the formula (110d)) are filtered off and the mother liquor is evaporated substantially to dryness in a rotary evaporator. A yellow precipitate forms from the residue, and is filtered off and washed with hexane. The yellowish powder gives, after recrystallization from ethyl acetate, 4.25 g of the compound of the formula

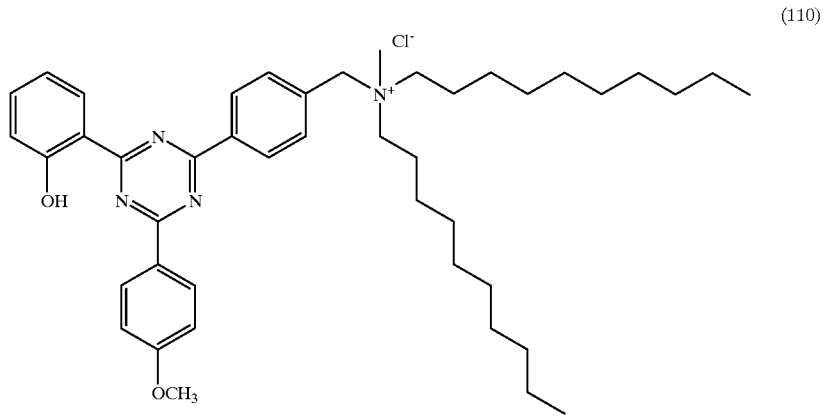
in the form of yellow flaky crystals (yield 29.7%).
Physical data:
Melting point 155–160° C. $^1$H-NMR ($C_6D_6$), δ in ppm: 13.04 (s, 1H, —OH), 8.51 (d, 1H, aromatic), 8.45 (d, 2H, aromatic), 8.31 (d, 2H, aromatic), 7.80 (d, 2H, aromatic), 7.13 (t, 1H, aromatic), 6.96 (d, 1H, aromatic), 6.75 (t, 1 H, aromatic) 6.66 (d, 2H, aromatic), 5.53 (s, 2H, PhCH$_2$NR$_3^+$), 3.36 (s, 3H, —OCH$_3$), 3.08 (m, 4H, —$^+$NCH$_2$R), 2.75 (s, 3H, —$^+$NCH$_3$),1.75–1.10 (m, 32H, aliphatic), 0.87 (t, 6H, —CH$_3$)
Equation:
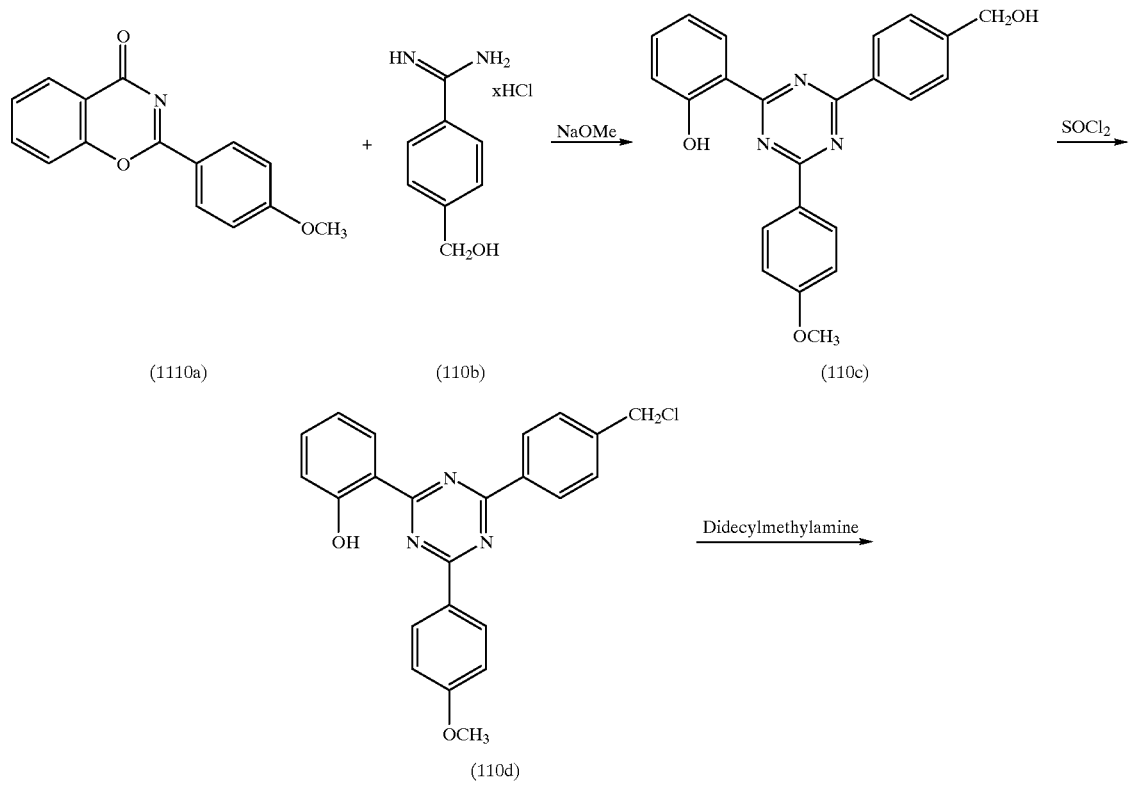

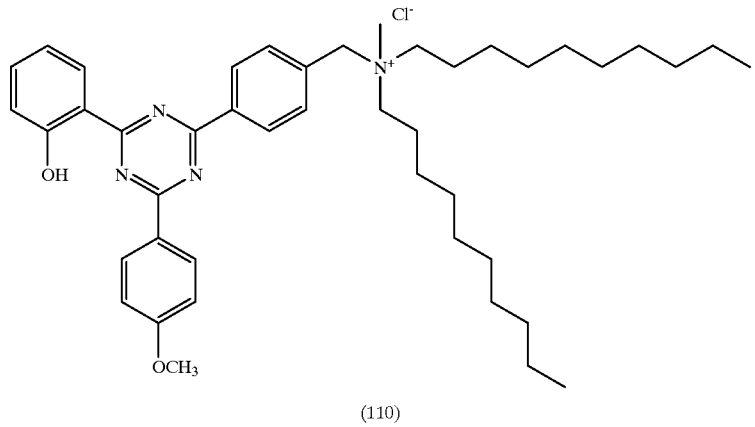

(110)

Use examples:

EXAMPLE 11 a. Preparation of liposomes

1–5 g of the compound of the formula (101a) (for the preparation, cf. Example 1) are dissolved in 100 ml of N-methylpyrrolidone (NMP). This solution is then added dropwise to 900 ml of 0.9% aqueous NaCl solution or is injected with a syringe, liposomes forming. The volume of the resulting liposome suspension is concentrated to 50–100 ml with the aid of a diafiltration apparatus (Ultrasette, Skan AG, Basle), so that the liposomes are correspondingly concentrated to 1–10%. The solvent is then exchanged, likewise with the aid of the diafiltration apparatus, by filtering further and at the same time replacing the volume of the filtrate removed by pure 0.9% NaCl solution. At least five times the volume of pure 0.9% NaCl solution, based on the concentrated liposome suspension, is used for the solvent exchange. At an initial NMP content of 10%, not more than 0.07% of NMP then still remain in the suspension. The residual content of NMP can be reduced as desired by increasing the volume of the 0.9% NaCl solution used for the exchange.

Alternatively, liposomes are prepared by initially again dissolving 1–5 g of the compound of the formula (101a) in 100 ml of solvent (NMP, ethanol or diethyl ether). The solution is then introduced into a round-bottomed flask and heated and the solvent is stripped off in vacuo using a rotary evaporator. 50–100 ml of 0.9% NaCl solution are now added to the resulting film on the inside wall of the flask, and the flask is then shaken. The liposomes formed as a result are then treated with ultrasound with the aid of an ultrasonic rod (Branson Model 250 Sonifier, Skan AG, Basle) for 10–60 minutes, which leads to a reduction in the size of the liposomes.

b. Determination of the diameter of the liposomes

The diameter of the liposomes is determined with the aid of photon correlation spectroscopy (ALV/monomode fibre compact goniometer system, ALV-Laser GmbH, Langen). For this, the liposome suspension is diluted to 0.02% to 0.1% and the autocorrelation function of the scattered light fluctuations is measured at four angles of scatter (30°, 60°, 90° and 120°). Average diffusion coefficients are obtained therefrom with the aid of CONTIN software, and in the case of a dependence on the angle, are extrapolated to the angle of scatter of 0°. The diameter of the liposomes is obtained from the resulting diffusion coefficients using the Stokes-Einstein relationship. For the liposomes of the compound of the formula (101a) prepared by the injection method, the following result is found:

$d=(220\pm40)$ nm.

This is regarded as evidence that liposomes are present. With the second method for liposome preparation, described under a., the diameter can be adjusted to between 1000 and 200 nm by varying the ultrasonic treatment time (10 to 60 minutes).

c. Spectral properties:

The maximum extinction of the compound of the formula (101a) is at a wavelength of 310 nm. At this wavelength, the extinction of a 1% solution at an optical layer thickness of 1 cm is:

$E(1\%, 1\text{ cm})=612.$

The half-intensity width of the absorption band is 58 nm.

d. Determination of the light protection factors:

Light protection factors (LPF) are determined by the method of Diffey and Robson (J. Soc. Cosmet. Chem. 40 (1989) 127). 2 $\mu$l of the formulation per $cm^2$ are thus applied to Transpore® tape (3M). The diffuse transmission (measurment using an integration sphere) is then measured in the spectral range between 290 and 400 nm against uncoated Transpore® tape and, for calculation of the sun protection factor, weighted with the sensitivity spectrum of the skin and the intensity spectrum of the sun. Nine measurements are carried out in each case, the highest and the lowest value of the resulting sun protection factors not being taken into account, so that the average is finally taken with seven measurement values. For a 5% liposome suspension of the compound of the formula (101a), the result is thus:

$LPF=8.6\pm1.7.$

EXAMPLE 12 a. Preparation of liposomes

The liposomes are prepared as described in Example 11a., but, instead of the compound of the formula (101a), the compound of the formula (101b) is used, and instead of NMP as the solvent for the injection, ethanol heated to 65° C. is used.

b. Determination of the diameter of the liposomes

The diameter of the liposomes is determined as described in Example 11b. For liposomes of the compound of the formula (101b), the value obtained is:

$$d=(190\pm30) \text{ nm}.$$

c. Spectral properties

The maximum extinction of the compound of the formula (101b) is at a wavelength of 310 nm. At this wavelength, the extinction of a 1% solution at an optical layer thickness of 1 cm is:

$$E(1\%, 1 \text{ cm})=601$$

The half-intensity width of the absorption band is 58 nm.

d. Determination of light protection factors

The light protection factor is determined in a manner analogous to that described in Example 11e. for the compound of the formula (101a). With a 5% suspension of the compound of the formula (101b), the value found is $$LPF=8.3\pm1.6.$$

EXAMPLE 13 a. Preparation of liposomes

The liposomes are prepared in a manner analogous to that described in Example 11a., with the difference that, instead of the compound of the formula (101a), the compound of the formula (102a) is used (for the preparation of the compound, cf. Example 2). The solvent used for the injection is ethanol or NMP.

b. Determination of the diameter of the liposomes

The diameter of the liposomes is determined as described in Example 11b. For liposomes of the compound of the formula (102a), the value obtained is:

$$d=(250\pm40) \text{ nm}.$$

c. Spectral properties

The maximum extinction of the compound of the formula (102a) is at a wavelength of 328 nm. At this wavelength, the extinction of a 1% solution at an optical layer thickness of 1 cm is:

$$E(1\%, 1 \text{ cm})=273.$$

The half-intensity width of the absorption band is 71 nm.

d. Determination of light protection factors

The light protection factor is determined in a manner analogous to that described in Example 11d. With a 5% suspension of the compound of the formula (102a), the value found is $$LPF=3.0\pm0.3.$$

EXAMPLE 14 a. Preparation of liposomes

The liposomes are prepared as described in Example 11a., with the difference that, instead of the compound of the formula (101a), the compound of the formula (102b) is used. The solvent used for the injection is ethanol or NMP.

b. Determination of the diameter of the liposomes

The diameter of the liposomes is determined as described in Example 11b. For liposomes of the formula (102b), the value obtained is:

$$d=(150\pm25) \text{ nm}.$$

c. Spectral properties

The maximum extinction of the compound of the formula (102b) is at a wavelength of 328 nm. At this wavelength, the extinction of a 1% solution at an optical layer thickness of 1 cm is:

$$E(1\%, 1 \text{ cm})=274.$$

The half-intensity width of the absorption band is 69 nm.

d. Determination of light protection factors

The light protection factor is determined in a manner analogous to that described in Example 11e. With a 5% suspension of the compound of the formula (102b), the value found is $$LPF=3.0\pm0.3.$$

EXAMPLE 15 a. Preparation of liposomes

The liposomes are prepared as described in Example 11a., with the difference that, instead of the compound of the formula (101a), the compound of the formula (104) is used (for the preparation of the compound, cf. Example 4). The solvent used for the injection is ethanol or NMP.

b. Determination of the diameter of the liposomes

The diameter of the liposomes is determined as described in Example 11b. For liposomes of the compound of the formula (104), the value obtained is:

$$d=(120\pm15) \text{ nm}.$$

c. Spectral properties

The maximum extinction of the compound of the formula (104) is at a wavelength of 303 nm. At this wavelength, the extinction of a 1% solution at an optical layer thickness of 1 cm is:

$$E(1\%, 1 \text{ cm})=654.$$

The half-intensity width of the absorption band is 39 nm.

d. Determination of light protection factors

The light protection factor is determined as described in Example 11e. With a 5% suspension of the compound of the formula (104), the value found is $$LPF=5.0\pm0.5.$$

EXAMPLE 16 a. Preparation of liposomes

The liposomes are prepared as described in Example 11a., with the difference that, instead of the compound of the formula (101a), the compound of the formula (105) is used (for the preparation of the compound, cf. Example 5). The solvent used for the injection is ethanol or NMP.

b. Determination of the diameter of the liposomes

The diameter of the liposomes is determined as described in Example 11b. For liposomes of the formula (105), the value obtained is:

$d=(150\pm25)$ nm.

c. Spectral properties

The maximum extinction of the compound of the formula (105) is at a wavelength of 328 nm. At this wavelength, the extinction of a 1% solution at an optical layer thickness of 1 cm is:

$E(1\%, 1\ cm)=215.$

The half-intensity width of the absorption band is 68 nm.

d. Determination of light protection factors

The light protection factor is determined as described in Example 11e. With a 5% suspension of the compound of the formula (105), the value found is $LPF=2.3\pm0.3.$

EXAMPLE 17 a. Preparation of liposomes

The liposomes are prepared as described in Example 11a., with the difference that, instead of the compound of the formula (101a), the compound of the formula (106) is used (for the preparation of the compound, cf. Example 6). The solvent used for the injection is ethanol or NMP.

b. Determination of the diameter of the liposomes

The diameter of the liposomes is determined as described in Example 11b. For liposomes of the formula (106), the value obtained is:

$d=(180\pm30)$ nm.

c. Spectral properties

The maximum extinction of the compound of the formula (106) is at a wavelength of 312 nm. At this wavelength, the extinction of a 1% solution at an optical layer thickness of 1 cm is:

$E(1\%, 1\ cm)=451.$

The half-intensity width of the absorption band is 50 nm.

d. Determination of light protection factors

The light protection factor is determined as described in Example 11e. With a 5% suspension of the compound of the formula (106), the value found is $LPF=5.6\pm0.7.$

EXAMPLE 18 a. Preparation of liposomes

The liposomes are prepared as described in Example 11a., with the difference that, instead of the compound of the formula (101a), the compound of the formula (107) is used (for the preparation of the compound, cf. Example 7). The solvent used for the injection is ethanol or NMP.

b. Determination of the diameter of the liposomes

The diameter of the liposomes is determined as described in Example 11b. For liposomes of the formula (107), the value obtained is:

$d=(980\pm130)$ nm.

c. Spectral properties

The maximum extinction of the compound of the formula (107) is at a wavelength of 313 nm. At this wavelength, the extinction of a 1% solution at an optical layer thickness of 1 cm is:

$E(1\%, 1\ cm)=347.$

The half-intensity width of the absorption band is 52 nm.

d. Determination of light protection factors

The light protection factor is determined as described in Example 11e. With a 5% suspension of the compound of the formula (107), the value found is $LPF=3.8\pm0.4.$

EXAMPLE 19 a. Preparation of liposomes

The liposomes are prepared as described in Example 11a., with the difference that, instead of the compound of the formula (101a), the compound of the formula (108) is used (for the preparation of the compound, cf. Example 8). The solvent used for the injection is ethanol or NMP.

b. Determination of the diameter of the liposomes

The diameter of the liposomes is determined as described in Example 11b. For liposomes of the compound of the formula (108), the value obtained is $d=(170\pm30)$ nm.

c. Spectral properties

The maximum extinction of the compound of the formula (108) is at a wavelength of 310 nm. At this wavelength, the extinction of a 1% solution at an optical layer thickness of 1 cm is:

$E(1\%, 1\ cm)=418.$

The half-intensity width of the absorption band is 53 nm.

d. Determination of light protection factors

The light protection factor is determined as described in Example 11e. With a 5% suspension of the compound of the formula (108), the value found is $LPF=4.8\pm0.5.$

EXAMPLE 20 a. Preparation of liposomes

The liposomes are prepared as described in Example 11a., with the difference that, instead of the compound of the formula (101a), the compound of the formula (109) is used (for the preparation of the compound, cf. Example 9). The solvent used for the injection is NMP.

b. Spectral properties

The maximum extinction of the compound of the formula (107) is at a wavelength of 339 nm. At this wavelength, the extinction of a 1% solution at an optical layer thickness of 1 cm is:

$E(1\%, 1\ cm) = 237.$ c. Determination of light protection factors

The light protection factor is determined as described in Example 11e. With a 5% suspension of the compound of the formula (109), the value found is $LPF = 5.5.$

EXAMPLE 21

Determination of the affinity of UV absorbers for hair by determination of the degree of extraction from formulations or solutions 10 ml of a 10 mmolar UV absorber solution and 1 g of strands of hair are shaken in a defined and reproducible manner in a glass vessel. The decrease in the concentration of the UV absorber in the test formulation or solution is determined after 30 and 60 minutes by means of a spectrophotometer (see Table 6). The degree of extraction determined in this way is a measure of the substantivity of the UV absorber or of the formulation which comprises it.

TABLE 6

Determination of the degree of extraction

| Compound of the formula | UV absorber employed | Degree of extraction [%] after 30 minutes | after 60 minutes |
|---|---|---|---|
| (110) | [structure] Cl⁻ | 74.0 | 92.0 |
| (108) | [structure] | 15.0 | 19.0 |

EXAMPLE 22

Preparation of a hair rinse:

| Composition | |
|---|---|
| UV absorber of the formula (110) | 1 g |
| Mixture of cetylstearyl alcohol and the addition product of 1 mol of cetylstearyl alcohol and 33 mol of ethylene oxide | 2 g |
| Monoethanolamide | 0.5 g |
| Xanthan gum | 0.8 g |

The individual components are mixed, preservative and perfume oil are added and the pH is then adjusted to 6.5 with dilute HCl.

A ready-to-use hair rinse which offers good and lasting UV protection for human hair is obtained in this way.

What is claimed is:

1. A method of protecting human hair from the damaging effect of UV radiation by treating human hair with a liposomogenic UV absorber comprising a hydrophilic head group (=Z), a spacer (=W), a UV chromophore (Q) having an absorption in the range from 285 to 400 nm and at least one hydrophobic tail group (=A), which has the formula

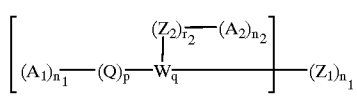 (1)

in which

A$_1$ and A$_2$ independently of one another are a hydrophobic radical;

Q is a UV chromophore;

W is an organic radical;

Z$_1$ and Z$_2$ independently of one another are a hydrophilic radical;

n$_1$ and n$_2$ independently of one another are a number from 0 to 4, where n$_1$=n$_2$=0 is not included;

p is 1 or 2;

q is a number from 0 to 3;

r$_1$ is 1 or 2;

r$_2$ is 0 or 1; and s$_1$ is a number from 1 to 3.

2. A method according to claim 1, wherein the UV chromophore Q in formula (1) is selected from the group consisting of (Q$_1$) cinnamic acid esters; and (Q$_2$) triazines derivatives.

3. A method according to claim 1, wherein the UV chromophore (Q$_1$) is derived from a cinnamic acid ester of the formula

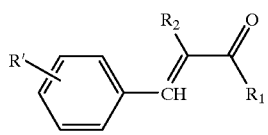 (2)

in which

R' is hydrogen, C$_1$–C$_4$alkyl; or C$_1$–C$_4$alkoxy;

R$_1$ is C$_1$–C$_4$alkoxy; and

R$_2$ is hydrogen; C$_1$–C$_4$alkyl; or —CN.

4. A method according to claim 1, wherein the UV chromophore (Q$_2$) is derived from an α-hydroxyphenyl-s-triazine compound of the formula

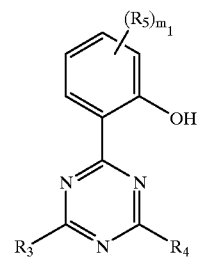 (3)

in which

R$_3$ and R$_4$ independently of one another are C$_1$–C$_5$alkyl; C$_1$–C$_{18}$alkyl which is substituted by hydroxyl, C$_1$–C$_5$alkoxy, C$_1$–C$_5$alkylthio, amino or C$_1$–C$_5$mono- or -dialkylamino; unsubstituted phenyl; or phenyl which is substituted by chlorine, hydroxyl, C$_1$–C$_{18}$alkyl and/or C$_1$–C$_{18}$alkoxy;

R$_5$ is C$_1$–C$_{18}$alkyl; C$_1$–C$_{18}$alkoxy; halogen; hydroxyl; a radical of the formula $$-(O-CH_2-CH_2-)_t-R_6;$$ (3a)

or a radical of the formula

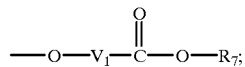 (3b)

R$_7$ is C$_1$–C$_5$alkyl or C$_1$–C$_5$alkoxy-C$_1$–C$_5$alkyl;

V$_1$ is a C$_1$–C$_4$alkylene radical;

m$_1$ is 0, 1 or 2;

t is 1 to 5;and

R$_6$ is hydrogen; or C$_1$–C$_5$alkyl.

5. A hair cosmetics preparation comprising at least 0.25 to 5% by weight, based on the total weight of the composition, of a liposomogenic UV absorber of the formula (1) and at least one auxiliary which is tolerated by the skin and hair.

6. A process for the treatment of human hair for protection from the damaging effect of UV radiation, which comprises treating the hair with a shampoo, a lotion, a gel or an emulsion for rinsing, before or after shampooing, before or after dyeing or bleaching, or before or after a permanent wave or a straightening operation, with a lotion, a foam or a gel for styling, with a lotion, a foam or a gel for brushing or for waving, with a hair lacquer or with a composition for a permanent wave or for straightening, or for dyeing or bleaching the hair, the shampoo, the lotion, the gel, the emulsion, the hair lacquer or the composition for a permanent wave comprising a liposomogenic UV absorber of the formula (1) as defined in claim 1.

* * * * *